United States Patent
Barnikow et al.

(10) Patent No.: US 8,573,190 B2
(45) Date of Patent: Nov. 5, 2013

(54) METHOD FOR HEATING A GAS SENSOR

(75) Inventors: Stefan Barnikow, Bad Abbach (DE); Johannes Scheuerer, Taufkirchen / Vils (DE)

(73) Assignee: Continental Automotive GmbH, Hannover (DE)

( * ) Notice: Subject to any disclaimer, the term of this patent is extended or adjusted under 35 U.S.C. 154(b) by 845 days.

(21) Appl. No.: 12/670,920

(22) PCT Filed: Jul. 24, 2008

(86) PCT No.: PCT/EP2008/059738
§ 371 (c)(1),
(2), (4) Date: May 14, 2010

(87) PCT Pub. No.: WO2009/016097
PCT Pub. Date: Feb. 5, 2009

(65) Prior Publication Data
US 2010/0218751 A1     Sep. 2, 2010

(30) Foreign Application Priority Data
Jul. 27, 2007 (DE) .......................... 10 2007 035 188

(51) Int. Cl.
*F01N 3/18* (2006.01)
*F02D 41/14* (2006.01)

(52) U.S. Cl.
USPC .................... 123/697; 123/142.5 E; 123/685; 60/300; 60/303

(58) Field of Classification Search
USPC .............. 123/142.5 E, 685, 697; 60/300, 303
See application file for complete search history.

(56) References Cited

U.S. PATENT DOCUMENTS

| | | | | |
|---|---|---|---|---|
| 3,869,597 A * | 3/1975 | Strange | ............. | 219/505 |
| 4,524,264 A * | 6/1985 | Takeuchi et al. | ............. | 219/497 |
| 5,111,792 A * | 5/1992 | Nagai et al. | ............. | 123/685 |
| 5,656,190 A * | 8/1997 | Aoki | ............. | 219/505 |
| 5,719,778 A * | 2/1998 | Suzumura et al. | ............. | 700/207 |
| 6,258,232 B1 * | 7/2001 | Hasegawa et al. | ............. | 204/424 |
| 6,921,883 B2 | 7/2005 | Kato et al. | ............. | 219/494 |
| 7,523,653 B2 * | 4/2009 | Smith et al. | ............. | 73/114.69 |
| 7,568,477 B2 | 8/2009 | Aoki | ............. | 123/676 |
| 8,240,127 B2 * | 8/2012 | Wahl et al. | ............. | 60/274 |
| 2009/0173326 A1 | 7/2009 | Aoki | ............. | 123/693 |
| 2009/0173327 A1 | 7/2009 | Aoki | ............. | 123/693 |

FOREIGN PATENT DOCUMENTS

| | | |
|---|---|---|
| DE | 102005063184 | 7/2007 |
| EP | 1239282 | 9/2002 |
| EP | 1413728 | 4/2004 |
| JP | 57200646 | 12/1982 |
| JP | 60164240 | 8/1985 |
| WO | 2005071247 | 8/2005 |

OTHER PUBLICATIONS

German Office Action for Application No. 10 2007 035 188.9 (4 pages), Feb. 22, 2008.
International Search Report for Application No. PCT/EP2008/059738 (8 pages), Oct. 27, 2008.

* cited by examiner

*Primary Examiner* — Erick Solis
(74) *Attorney, Agent, or Firm* — King & Spalding L.L.P.

(57) ABSTRACT

In a method for heating a gas sensor (1), in particular an exhaust gas sensor for an exhaust system (5) of a motor vehicle (7), a temperature of the gas sensor (1) is determined and the heating process is influenced as a function of the temperature.

16 Claims, 3 Drawing Sheets

METHOD FOR HEATING A GAS SENSOR

CROSS-REFERENCE TO RELATED APPLICATIONS

This application is a U.S. National Stage Application of International Application No. PCT/EP2008/059738 filed Jul. 24, 2008, which designates the United States of America, and claims priority to German Application No. 10 2007 035 188.9 filed Jul. 27, 2007, the contents of which are hereby incorporated by reference in their entirety.

TECHNICAL FIELD

The invention relates to a method for heating a gas sensor, in particular an exhaust sensor for an exhaust system of a motor vehicle.

BACKGROUND

The exhaust gases from a motor vehicle's internal combustion engine have to be treated to ensure compliance with legally stipulated limits. The exhaust gases are for that purpose examined using exhaust sensors. Said exhaust sensors have to be kept at a specified operating temperature during operation. The exhaust sensors are for that purpose electrically heated by means of a temperature-regulated heater.

The exhaust sensors should be available ready to operate as soon as possible after the combustion engine starts and, to that end, should reach their operating temperature as quickly as possible. A voltage applied to a sensor heater is for that purpose increased as much as possible. The voltage applied to a sensor heater adheres in the prior art to a pre-fixed scheme. Switchover to temperature-regulated heating does not take place until the exhaust sensor's operating temperature has been reached. The scheme employed for the voltage curve on the sensor heater is a compromise between reaching the exhaust sensor's operational readiness as quickly as possible and preventing the exhaust sensor's destruction due to temperature changes that are too fast. To prevent the sensor's destruction, a maximum permissible temperature gradient in the exhaust sensor must not be exceeded, for example.

The fixed scheme for the heating-voltage curve takes no account of individual characteristics of the heating-voltage source or of the sensor heater employed. Because said characteristics vary in practice, the scheme for the heating-voltage curve must be devised such that the maximum permissible thermal load on the exhaust sensor will not be exceeded for any combinations of exhaust sensors and voltage-generating means. The disadvantage of that approach is that for most combinations of exhaust sensor and voltage-generating means the exhaust sensor is heated more slowly than is possible. Treatment for the exhaust gas after the combustion engine starts is consequently available later than is possible. In order nonetheless to fulfill the legal requirements placed on exhaust limits, the combustion engine's other systems must also be designed allowing for an appropriate reserve.

DE 10 2005 063 184 A1 describes a method for heating a gas sensor. The gas sensor is therein heated by means of pre-fixed heating voltages until measuring readiness has been attained. One or more switchover instants between the pre-fixed heating voltages can be ascertained as a function of the gas sensor's temperature. Changeover to a temperature-regulated heating strategy takes place when measuring readiness has been attained.

EP 1 239 282 A2 likewise describes a method for heating a gas sensor. The gas sensor is heated at a decreasing heating rate until the target temperature has been reached. Changeover to a regulated heating strategy takes place when the target temperature has been reached.

SUMMARY

According to various embodiments, an improved method for heating an exhaust sensor in a motor vehicle's exhaust system is disclosed.

According to an embodiment, in a method for heating a gas sensor, in particular an exhaust sensor for an exhaust system of a motor vehicle, a temperature of the gas sensor is ascertained, with a future heating process being influenced as a function of the temperature.

According to a further embodiment, a temperature gradient can be ascertained from the temperature of the gas sensor. According to a further embodiment, the ascertained temperature or temperature gradient can be compared with a predefined limit and the future heating process can be influenced as a function of the comparison. According to a further embodiment, the method can be be implemented if the temperature of the gas sensor is below a predefined temperature. According to a further embodiment, an operating temperature of the gas sensor can be used as the predefined temperature. According to a further embodiment, a heating output for heating the gas sensor can be influenced in order to set a desired temperature gradient. According to a further embodiment, the gas sensor can be heated to a predefined temperature via a pilot control, wherein heating of the gas sensor is regulated as a function of the temperature of the gas sensor when the predefined temperature has been reached. According to a further embodiment, for the pilot control at least one pilot-control value can be used with which the gas sensor is heated to the predefined temperature, wherein at least one temperature gradient of the gas sensor can be ascertained while the sensor is being heated to the predefined temperature, wherein the ascertained temperature gradient is compared with a predefined limit, and wherein a corrected pilot-control value is ascertained from the comparison, which value is used in a following heating process that has pilot controlling. According to a further embodiment, the heating process can be divided into a first segment and a second segment, wherein the gas sensor is heated via the pilot control during the first segment, wherein the gas sensor is also heated via a pilot control during the second segment, wherein a temperature gradient of the gas sensor is ascertained during the second segment, and wherein the ascertained temperature gradient is used during pilot controlling in a first segment of a new heating process. According to a further embodiment, the heating process can be divided into a first segment and a second segment, wherein the gas sensor is heated via the pilot control during the first segment, wherein the gas sensor is also heated via a pilot control during the second segment, wherein a temperature gradient of the gas sensor is ascertained during the second segment, and wherein the ascertained temperature gradient is used during pilot controlling in a second segment of a new heating process. According to a further embodiment, a maximum temperature gradient can be ascertained as the temperature gradient. According to a further embodiment, the heating process can be divided into a first segment and a second segment, wherein the gas sensor is heated via a pilot control during the first segment, wherein heating of the gas sensor is regulated during the second segment as a function of the temperature gradient, wherein a temperature gradient of the gas sensor is ascertained during the second segment, and wherein the ascertained temperature gradient is used during pilot controlling in a first segment of a new heating process.

According to a further embodiment, a lambda probe can be used as the gas sensor. According to a further embodiment, a nitrogen-oxide sensor can be used as the gas sensor. According to a further embodiment, a carbon-dioxide sensor can be used as the gas sensor.

According to another embodiment, in a method for ascertaining a pre-control value for heating a gas sensor for an exhaust system of a motor vehicle, the gas sensor is heated to a predefined temperature using at least one pre-control value, wherein a temperature gradient of the gas sensor is ascertained while the gas sensor is being heated to the predefined temperature, wherein the temperature gradient is compared with a predefined limit, and wherein a corrected pilot-control value is ascertained from the comparison, which value is used in a following heating process.

According to a further embodiment, a maximum temperature gradient can be ascertained as the temperature gradient. According to a further embodiment, an operating temperature of the gas sensor can be used as the predefined temperature. According to a further embodiment, heating can be divided into at least two segments, wherein at least two different pilot-control values are used for the two segments, wherein at least one temperature gradient is ascertained during heating, wherein the ascertained temperature gradient is compared with at least one limit, and wherein the pilot-control values are checked and, if necessary, adjusted on the basis of the comparison.

BRIEF DESCRIPTION OF THE DRAWINGS

The invention is explained in more detail below with the aid of exemplary embodiments and with reference to the attached drawings, of which

DETAILED DESCRIPTION

Figure 1:
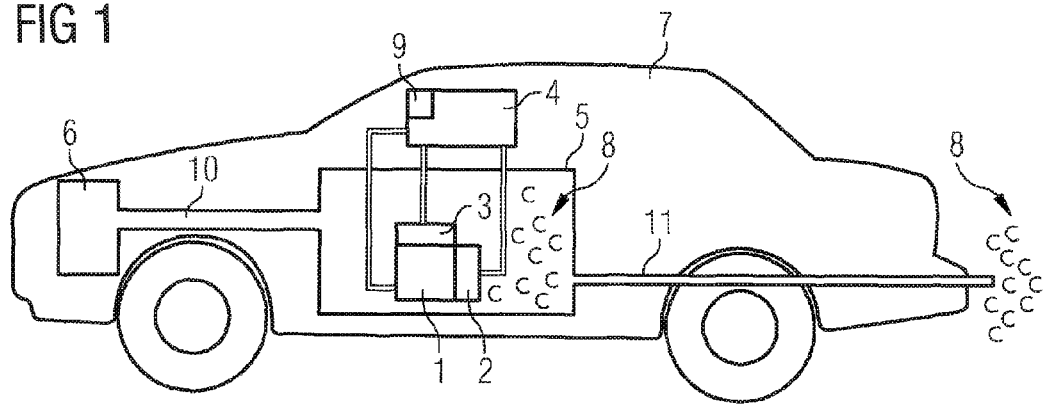
FIG. 1 is a schematic of an exhaust system of a motor vehicle having an exhaust sensor with a heater and a device for determining the exhaust sensor's temperature.

An advantage of the various embodiments is that the exhaust sensor is heated close to the maximum possible temperature gradient. The heating process for the exhaust sensor is shortened thereby. The exhaust sensor will consequently reach its operational readiness faster if heating of the exhaust sensor was previously limited by the exhaust sensor's maximum permitted temperature gradient. In the design of the other components of the motor vehicle and combustion engine it will then be possible to proceed on the basis of faster operational readiness on the part of the exhaust sensor. Fewer reserves will accordingly have to be taken into account in the combustion engine's design.

The temperature of the exhaust sensor is already measured according to various embodiments during at least a part of the heating time. That will require no additional effort since according to conventional systems the exhaust sensor is in any case fitted with suitable equipment for ascertaining the temperature.

In an embodiment, a temperature gradient is ascertained from the temperature of the exhaust sensor. In an embodiment, the temperature or temperature gradient of the exhaust sensor is compared with a predefined limit and the heating process adjusted accordingly. That is done in an embodiment by changing a heating output.

In an embodiment, the exhaust sensor is heated via a pilot control using a pilot-control value. The pilot-control value can be adjusted as a function of an ascertained temperature or temperature gradient of the exhaust sensor and the adjusted pilot-control value used in a following heating process.

In a further embodiment, the heating process is divided into at least two segments during which the exhaust sensor is heated by means of a pilot control using two different pilot-control values. At least one temperature gradient of the exhaust sensor is ascertained during at least one of the segments. The pilot-control value of the first segment or the pilot-control value of the second segment or both pilot-control values is/are preferably adjusted by means of the ascertained temperature gradient and the adjusted pilot-control values used in a following heating process. In a further embodiment, not only is a temperature gradient of the exhaust sensor ascertained and used for adjusting the heating process; the exhaust sensor's maximum temperature gradient having occurred during the heating process is ascertained.

In a further embodiment, the exhaust sensor is heated in a regulated manner, with the exhaust sensor's temperature gradient being used as the regulating variable. In a further embodiment, the heating process is subdivided into at least two segments, with the exhaust sensor being heated via a pilot control during the first segment and heating of the exhaust sensor being regulated during the second segment of the heating process, with a temperature gradient of the exhaust sensor being used as the regulating variable. A maximum temperature gradient ascertained during the second segment can preferably serve also to adjust the pilot-control value used during the first segment of a further heating process.

In particularly embodiments, the exhaust sensor is a lambda probe, a nitrogen-oxide sensor, or a carbon-dioxide sensor.

FIG. 1 is a schematic of a motor vehicle 7 having a combustion engine 6 and an exhaust system 5. The exhaust gas 8 arising in the combustion engine 6 enters the exhaust system 5 on the input side 10 of the exhaust system 5. The exhaust gas 8 exits the exhaust system 5 on the output side 11 of the exhaust system 5. Inside the exhaust system 5 is an exhaust sensor 1. The exhaust sensor 1 is linked to a heater 2 for heating the exhaust sensor 1. The exhaust sensor 1 is linked further to a thermometer 3 for determining the temperature of the exhaust sensor 1. The exhaust sensor 1, the heater 2 for heating the exhaust sensor 1, and the thermometer 3 for determining the temperature of the exhaust sensor 1 are linked to an evaluation and control unit 4. The evaluation and control unit 4 evaluates the temperature of the exhaust sensor 1 ascertained by the thermometer 3 and adjusts the heating output of the heater 2 in accordance with a method according to various embodiments. The evaluation and control unit 4 is linked to a non-volatile data memory 9 for storing pilot-control values. The evaluation and control unit 4 can be implemented as a separate unit. The evaluation and control unit 4 can, though, also be integrated in an electronic engine control of the combustion engine 6.

Figure 2:
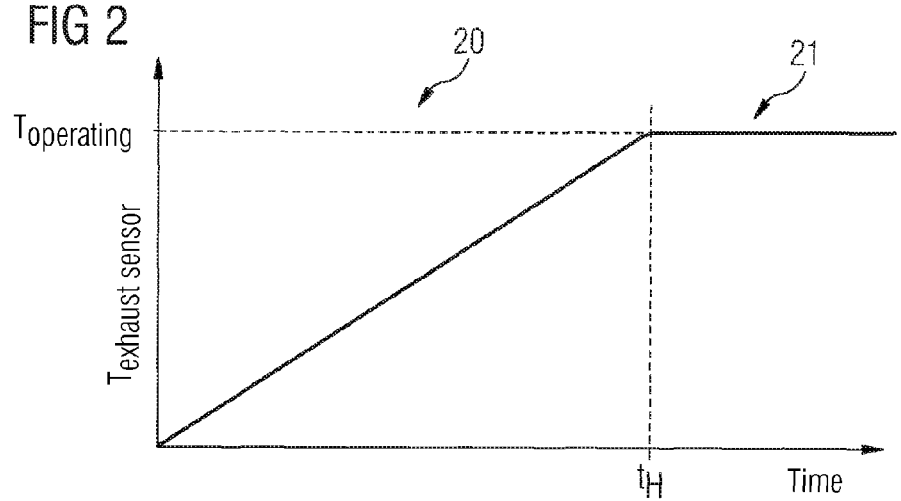
FIG. 2 is a schematic of the curve of an exhaust sensor's temperature during a heating process comprising one segment.

FIG. 2 shows schematically the temperature $T_{exhaust\ sensor}$ of the exhaust sensor 1 as a function of the time having elapsed since the combustion engine 6 started, with the exhaust sensor 1 being heated according to a method comprising a single segment 20. The temperature $T_{exhaust\,sensor}$ of the exhaust sensor 1 is plotted on the y-axis. The time having elapsed since the combustion engine 6 started is plotted on the x-axis. The exhaust sensor 1 is heated during a first time segment 20 by means of a heater 2 and the temperature $T_{exhaust\,sensor}$ of the exhaust sensor rises. After a time $t_H$, the temperature of the exhaust sensor has reached a predefined operating temperature $T_{operating}$.

Said operating temperature $T_{operating}$ of the exhaust sensor 1 can be, for example, 1,000° C. to 1,200° C. At that moment a second time segment 21 begins during which the evaluation and control unit 4 keeps the exhaust sensor 1 in regulated normal mode at a constant operating temperature $T_{operating}$.

Figure 4:
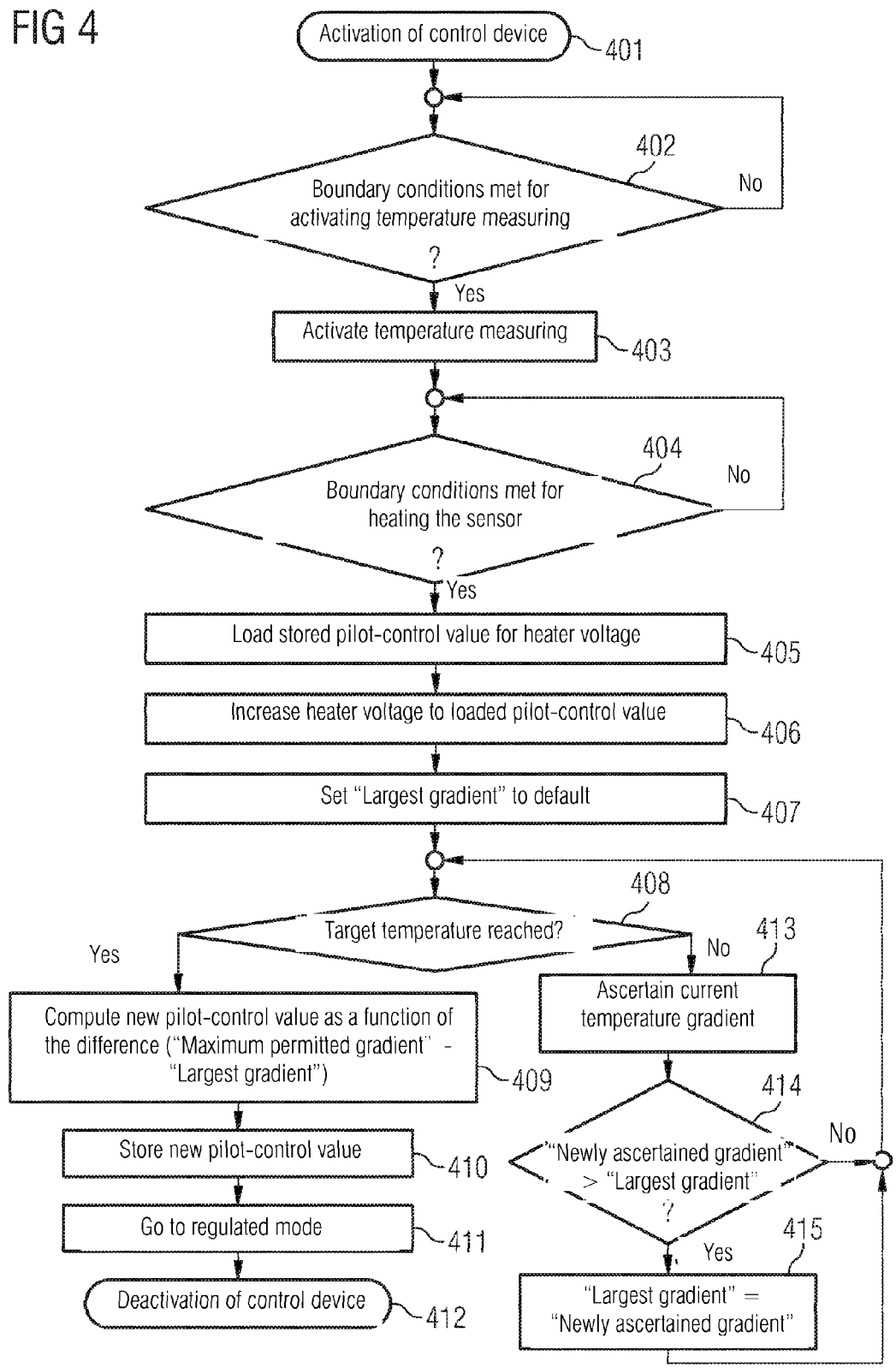
FIG. 4 is a schematic flowchart of a method for heating the exhaust sensor by means of a pilot control according to various embodiments.
Figure 5:
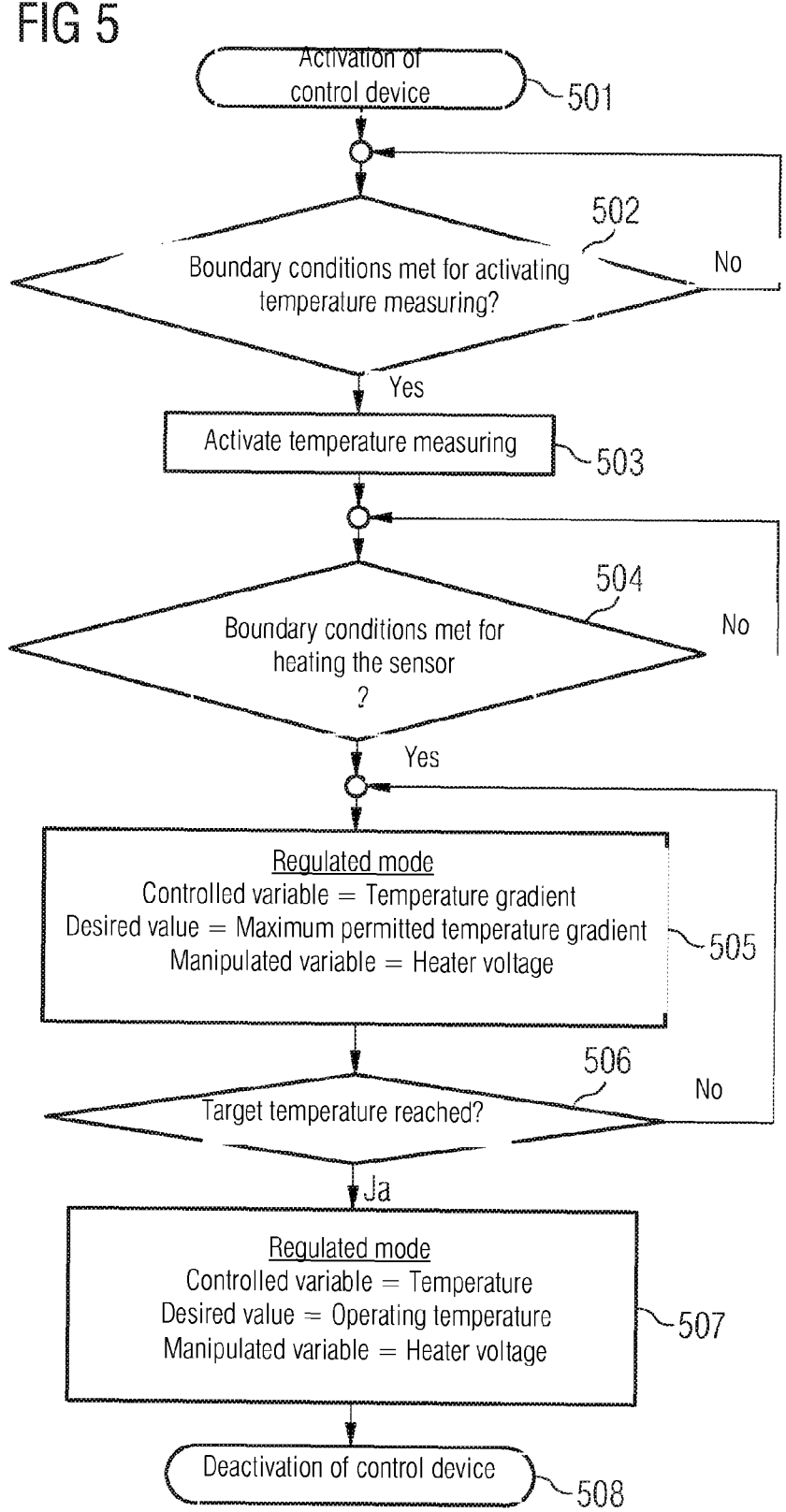
FIG. 5 is a schematic flowchart of an method for heating the exhaust sensor in a regulated mode according to various embodiments.

The evaluation and control unit 4 can heat the heater 2 of the exhaust sensor 1 via a pilot control during the heating period 20, as shown in FIG. 4. The evaluation and control unit 4 can, though, also regulate the heating output of the heater 2 of the exhaust sensor 1 during the heating period 20, as shown in FIG. 5. Both variants are explained below. During regulated normal mode 21, the evaluation and control unit 4 regulates the heating output of the heater 2 of the exhaust sensor 1 using the temperature $T_{exhaust\,sensor}$ of the exhaust sensor 1.

Figure 3:
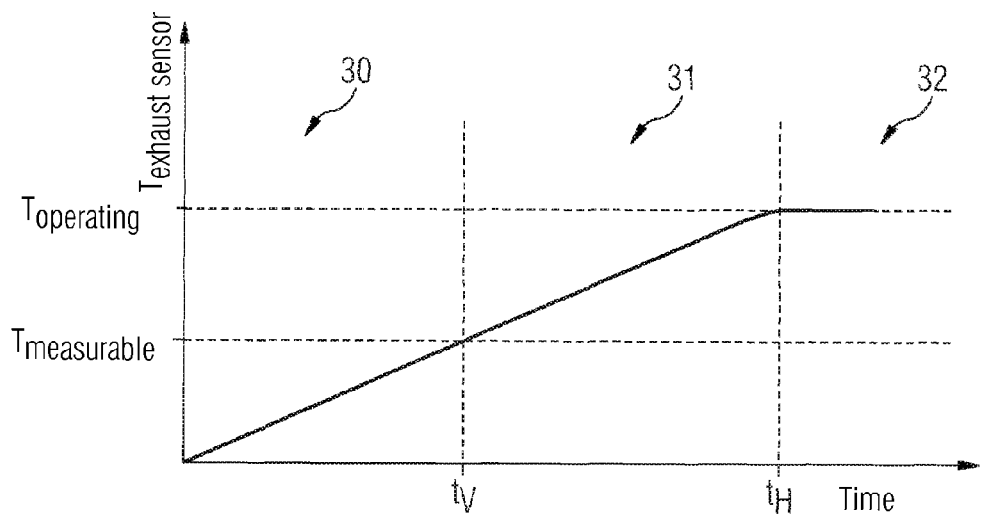
FIG. 3 is a schematic of the curve of an exhaust sensor's temperature during a heating process comprising two segments.

FIG. 3 is a schematic of the curve of the temperature $T_{exhaust\,sensor}$ of the exhaust sensor 1 during a heating operation performed on the exhaust sensor 1 after the combustion engine 6 has started. The temperature $T_{exhaust\,sensor}$ of the exhaust sensor 1 is plotted on the y-axis. The time having elapsed since the combustion engine 6 started is plotted on the x-axis. The temperature curve shown of the exhaust sensor 1 comprises three segments 30, 31, 32. During a first segment 30, the temperature $T_{exhaust\,sensor}$ of the exhaust sensor 1 is below a temperature $T_{measurable}$ as of which measuring the temperature $T_{exhaust\,sensor}$ of the exhaust sensor 1 by means of the thermometer 3 becomes possible. During said segment 30, the evaluation and control unit 4 controls the heating output of the heater 2 of the exhaust sensor 1 via a pilot control using pre-fixed pilot-control values for the heating output of the heater 2. After a time $t_V$, the temperature of the exhaust sensor reaches a temperature $T_{measurable}$ as of which measuring the temperature $T_{exhaust\,sensor}$ of the exhaust sensor 1 becomes possible. Said temperature $T_{measurable}$ can be, for example, 450° C. The first time segment 30 is followed immediately by a second time segment 31 during which the temperature $T_{exhaust\,sensor}$ of the exhaust sensor 1 is still below an operating temperature $T_{operating}$. During the second time segment 31, the evaluation and control unit 4 can, as shown in FIG. 4, control the heating output of the heater 2 of the exhaust sensor 1 via a pilot control. During the second time segment 31, the evaluation and control unit 4 can, though, as shown in FIG. 5, also regulate the heating output of the heater 2 using a temperature gradient of the exhaust sensor 1. The exhaust sensor 1 can be heated faster during the second time segment 31 than during the first time segment 30. The exhaust sensor 1 can, though, be heated more slowly during the second time segment 31 than during the first time segment 30. The temperature $T_{exhaust\,sensor}$ of the exhaust sensor 1 reaches an operating temperature $T_{operating}$ on expiration of a second time $t_H$ since the combustion engine 6 started. Said operating temperature $T_{operating}$ of the exhaust sensor 1 can be, for example, 1,000° C. to 1,200° C. At that moment a third time segment 32 begins during which the evaluation and control unit 4 regulates the heating output of the heater 2 of the exhaust sensor 1 such that the temperature $T_{exhaust\,sensor}$ of the exhaust sensor will remain the same as the operating temperature $T_{operating}$. The temperature $T_{exhaust\,sensor}$ of the exhaust sensor 1 supplied by the thermometer 3 therein serves as the regulating variable and the heating output of the heater 2 as the manipulated variable.

FIG. 4 is a schematic flowchart of a method for heating the exhaust sensor 1 wherein the heater 2 of the exhaust sensor 1 is driven via a pilot control. In the method shown, the heating process of the exhaust sensor 1 comprises just one time segment as in FIG. 2. The process starts at step 401 with activating of the evaluation and control unit 4. A check is then performed at step 402 to establish whether the boundary conditions for activating temperature measuring by means of the thermometer 3 have been met. Said boundary conditions include, inter alia, completed calibrating of the thermometer 3 at room temperature. The process will keep returning to a repeat check at step 402 if the boundary conditions have not yet been met. The process will continue at step 403 with activating of temperature measuring as soon as the boundary conditions have been met. The thermometer 3, which can be embodied as, for example, a 50-kΩ NTC resistor, is used for temperature measuring. A check is then performed at step 404 to establish whether the boundary conditions for heating the exhaust sensor 1 have been met. Said boundary conditions include, inter alia, that the exhaust sensor 1 be free from condensate. That can be checked by means of, for example, a humidity sensor. The process will keep returning to a repeat check at step 404 if said boundary conditions have not yet been met. The process will continue at step 405 when the boundary conditions have been met. At step 405, the evaluation and control unit 4 loads a stored pilot-control value for the heating voltage of the heater 2 from the non-volatile data memory 9. The evaluation and control unit 4 then at step 406 sets the heating voltage of the heater 2 to the pilot-control value loaded at preceding step 405, whereupon the exhaust sensor 1 starts being heated. That corresponds to the time segment 20 in FIG. 2 or the time segment 31 in FIG. 3. At step 407, the evaluation and control unit 4 initiates the value of the largest hitherto observed temperature gradient of the exhaust sensor 1 with a start value, for example the value 0. At step 408, the temperature $T_{exhaust\,sensor}$ of the exhaust sensor 1 is measured with the aid of the thermometer 3. The evaluation and control unit 4 then checks whether the measured temperature $T_{exhaust\,sensor}$ of the exhaust sensor 1 corresponds to its operating temperature $T_{operating}$. The heating process must continue for as long as that is not the case. A temperature gradient of the exhaust sensor 1 is for that purpose ascertained at step 413 from the temperature $T_{exhaust\,sensor}$ of the exhaust sensor 1 ascertained at step 408. A check is performed at step 414 to establish whether the temperature gradient ascertained at step 413 is larger than the largest hitherto observed temperature gradient. The process will continue at step 408 if it is not. If, though, the newly ascertained gradient is larger than the largest hitherto observed temperature gradient, the newly ascertained temperature gradient will at step 415 be established as the largest hitherto observed temperature gradient. The process will then continue at step 408.

The process will continue at step 409 as soon as the check performed at step 408 shows that the temperature $T_{exhaust\,sensor}$ of the exhaust sensor 1 ascertained by the thermometer 3 corresponds to the operating temperature $T_{operating}$ of the exhaust sensor 1. The difference between the largest temperature gradient of the exhaust sensor 1 observed during the heating process and the largest permitted temperature gradient of the exhaust sensor 1 is formed at step 409. A new pilot-control value for the heater 2 of the exhaust sensor 1 is computed from said difference. If the largest observed temperature gradient of the exhaust sensor 1 is below the maximum permitted temperature gradient of the exhaust sensor 1, the pilot-control value will be increased above the old pilot-control value by a predefined value, for example by 1% of the previous pilot-control value. If, conversely, the largest observed temperature gradient of the exhaust sensor 1 was above the maximum permitted temperature gradient of the exhaust sensor 1, the new pilot-control value will be decreased below the old pilot-control value by a predefined value, for example by 2% of the pilot-control value. The evaluation and control unit 4 stores the new pilot-control value in the non-volatile data memory for pilot-control values 9 at step 410. The evaluation and control unit 4 continues heating the exhaust sensor 1 in regulated normal mode at step 411. Said regulated normal mode corresponds to step 507, described below, in FIG. 5 and to the time segments 21 and 32 in FIGS. 2 and 3. The evaluation and control unit 4 will be deactivated at step 412 as soon as the combustion engine 6 is to be turned off. The process will be repeated again starting at step 401 the next time the combustion engine starts, with the newly ascertained pilot-control value being used starting from step 405.

FIG. 5 shows another preferred embodiment of a method for heating a gas sensor 1. What can be seen is a schematic flowchart of a method for heating the exhaust sensor 1 by means of regulating. The method begins at step 501 with activating of the evaluation and control unit 4 after the combustion engine 6 starts. Steps 502, 503, and 504 that follow correspond to the method steps 402, 403, and 404 that have already been described. The exhaust sensor 1 starts being heated, regulated by the evaluation and control unit 4 at step 505. Step 505 is executed during time segment 20 in FIG. 2 or time segment 31 in FIG. 3. What serves as the regulating variable is the temperature gradient of the exhaust sensor 1 obtained by measuring its temperature $T_{exhaust\ sensor}$ with the aid of the thermometer 3. The maximum permitted temperature gradient of the exhaust sensor 1 is used as the desired value for regulating. The heating voltage applied to the heater 2 is used as the manipulated variable for regulating. A check is performed at step 506 to establish whether the temperature $T_{exhaust\ sensor}$ of the exhaust sensor 1 measured with the aid of the thermometer 3 corresponds yet to the operating temperature $T_{operating}$ of the exhaust sensor 1. Regulated heating of the exhaust sensor 1 at step 505 continues for as long as that is not the case. The evaluation and control unit 4 continues heating the exhaust sensor 1 at step 507 in regulated normal mode as soon as the target temperature of the exhaust sensor 1 has been reached. Said regulated normal mode corresponds to above-described step 411 in FIG. 4 and to the time segments 21 and 32 in FIGS. 2 and 3. The temperature $T_{exhaust\ sensor}$ of the exhaust sensor 1 ascertained with the aid of the thermometer 3 serves as the regulating variable in said regulated normal mode. The desired value for regulating is represented by the operating temperature $T_{operation}$ of the exhaust sensor 1. The heating voltage applied to the heater 2 is used as the manipulated variable. The regulated normal mode at step 507 continues until the combustion engine 6 is to be turned off. The evaluation and control unit 4 is then deactivated at step 508, marking the end of the method.

If the thermometer 3 of the exhaust sensor 1 only permits the temperature $T_{exhaust\ sensor}$ of the exhaust sensor 1 to be determined above a minimum temperature $T_{measurable}$ of the exhaust sensor 1, the heating process of the exhaust sensor 1 can be divided into two time segments, as shown in FIG. 3. During the first time segment 30, the exhaust sensor 1 is heated without measuring of the temperature $T_{exhaust\ sensor}$ of the exhaust sensor 1 with the aid of a pilot control. A first pilot-control value is used therefor. The heating process of the exhaust sensor 1 continues at a second time segment 31 as soon as the temperature of the exhaust sensor 1 is above the temperature $T_{measurable}$ as of which measuring the temperature $T_{exhaust\ sensor}$ of the exhaust sensor 1 becomes possible. The exhaust sensor 1 can be heated via a pilot control in said time segment 31, as is shown at steps 405 to 415 in FIG. 4. The exhaust sensor 1 can, though, also be heated during the second time segment 31 with the aid of regulating, as is shown at steps 505 to 508 in FIG. 5. In both cases a temperature gradient of the exhaust sensor 1 ascertained at the start of the time segment 31 can be used to adjust the first pilot-control value employed during the time segment 30. Knowledge about the correlations between the temperature gradients during the first time segment 30 and second time segment 31 can also be used to adjust the pilot-control value employed during the first time segment 30.

What is claimed is:

1. A method for heating a gas sensor on successive start-ups, comprising the steps of:
   ascertaining a first temperature of the gas sensor during a first start-up;
   comparing the ascertained first temperature to a pre-defined value;
   if the ascertained temperature is less than the pre-defined value, heating the gas sensor based at least in part on a first pilot-control value;
   ascertaining a second temperature of the gas sensor;
   calculating a temperature gradient based on the ascertained first temperature and the ascertained second temperature;
   comparing the calculated temperature gradient to a pre-defined limit;
   if the calculated temperature gradient is less than the pre-defined limit, setting the pilot-control value at a higher second value for a second start-up; and
   if the calculated temperature gradient is greater than the predefined limit, setting the pilot-control value at a lower second value for a second start-up.

2. The method according to claim 1, wherein an operating temperature of the gas sensor is used as the predefined temperature.

3. The method according to claim 1, wherein a heating output for heating the gas sensor is influenced in order to set a desired temperature gradient.

4. The method according to claim 1, wherein the gas sensor is heated to a predefined temperature via a pilot control,
   wherein heating of the gas sensor is regulated as a function of the temperature of the gas sensor when the predefined temperature has been reached.

5. The method according to claim 4,
   wherein the heating process is divided into a first segment and a second segment,
   wherein the gas sensor is heated via the pilot control during the first segment,
   wherein the gas sensor is also heated via a pilot control during the second segment,
   wherein a temperature gradient of the gas sensor is ascertained during the second segment, and
   wherein the ascertained temperature gradient is used during pilot controlling in a first segment of a new heating process.

6. The method according to claim 4,
   wherein the heating process is divided into a first segment and a second segment,
   wherein the gas sensor is heated via the pilot control during the first segment,
   wherein the gas sensor is also heated via a pilot control during the second segment, wherein a temperature gradient of the gas sensor is ascertained during the second segment, and
wherein the ascertained temperature gradient is used during pilot controlling in a second segment of a new heating process.

7. The method according to claim 1, wherein a maximum temperature gradient is ascertained as the temperature gradient.

8. The method according to claim 1,
wherein the heating process is divided into a first segment and a second segment,
wherein the gas sensor is heated via a pilot control during the first segment,
wherein heating of the gas sensor is regulated during the second segment as a function of the temperature gradient,
wherein a temperature gradient of the gas sensor is ascertained during the second segment, and
wherein the ascertained temperature gradient is used during pilot controlling in a first segment of a new heating process.

9. The method according to claim 1, wherein a lambda probe is used as the gas sensor.

10. The method according to claim 1, wherein a nitrogen-oxide sensor is used as the gas sensor.

11. The method according to claim 1, wherein a carbon-dioxide sensor is used as the gas sensor.

12. A method for ascertaining a pre-control value for heating a gas sensor for an exhaust system of a motor vehicle, comprising the steps of:

heating the gas sensor to a predefined temperature using at least one pre-control value,
wherein a temperature gradient of the gas sensor is ascertained while the gas sensor is being heated to the predefined temperature,
wherein the temperature gradient is compared with a predefined limit, and
wherein a corrected pilot-control value is ascertained from the comparison, which value is used in a following heating process.

13. The method according to claim 12, wherein a maximum temperature gradient is ascertained as the temperature gradient.

14. The method according to claim 12, wherein an operating temperature of the gas sensor is used as the predefined temperature.

15. The method according to claim 12,
wherein heating is divided into at least two segments,
wherein at least two different pilot-control values are used for the two segments,
wherein at least one temperature gradient is ascertained during heating,
wherein the ascertained temperature gradient is compared with at least one limit, and
wherein the pilot-control values are checked and, if necessary, adjusted on the basis of the comparison.

16. The method according to claim 1, wherein the gas sensor is an exhaust sensor for an exhaust system of a motor vehicle.

* * * * *